US008282927B2

(12) United States Patent
Brown et al.

(10) Patent No.: US 8,282,927 B2
(45) Date of Patent: Oct. 9, 2012

(54) IMMUNOGLOBULIN FRACTION AND PROCESS THEREFOR

(75) Inventors: Andrew Brown, Cobram (AU); Peter Hobman, Melbourne (AU); Richard Paine, Diamond Creek (AU); Michelle Rowney, Port Campbell (AU)

(73) Assignee: Murray Goulburn Co-Operative Co Limited, Brunswick (AU)

( * ) Notice: Subject to any disclaimer, the term of this patent is extended or adjusted under 35 U.S.C. 154(b) by 898 days.

(21) Appl. No.: 11/920,198

(22) PCT Filed: May 10, 2006

(86) PCT No.: PCT/AU2006/000607
§ 371 (c)(1),
(2), (4) Date: Feb. 23, 2009

(87) PCT Pub. No.: WO2006/119560
PCT Pub. Date: Nov. 16, 2006

(65) Prior Publication Data
US 2009/0214567 A1    Aug. 27, 2009

(30) Foreign Application Priority Data

May 10, 2005    (AU) .............................. 2005902372

(51) Int. Cl.
*A61K 39/00* (2006.01)
*A61K 35/20* (2006.01)
(52) U.S. Cl. ..................................... 424/157.1; 424/535
(58) Field of Classification Search .................. None
See application file for complete search history.

(56) References Cited

U.S. PATENT DOCUMENTS

| | | | |
|---|---|---|---|
| 5,179,197 A | | 1/1993 | Uchida et al. |
| 5,747,031 A | * | 5/1998 | Ruch et al. .................. 424/130.1 |
| 5,756,680 A | | 5/1998 | Ahmed et al. |
| 5,780,028 A | * | 7/1998 | Graham ....................... 424/130.1 |
| 5,866,418 A | | 2/1999 | Ballard et al. |
| 5,871,731 A | * | 2/1999 | Sprotte et al. .............. 424/130.1 |
| 6,010,698 A | | 1/2000 | Kussendrager et al. |
| 6,096,870 A | | 8/2000 | Mozaffar et al. |
| 6,616,927 B2 | * | 9/2003 | Hodgkinson et al. ...... 424/157.1 |
| 2005/0245729 A1 | * | 11/2005 | Noel ........................... 530/387.1 |
| 2009/0214567 A1 | * | 8/2009 | Brown et al. .............. 424/157.1 |
| 2010/0272708 A1 | * | 10/2010 | Juneau et al. ............... 424/130.1 |
| 2010/0303830 A1 | * | 12/2010 | Bruessow et al. .......... 424/164.1 |

FOREIGN PATENT DOCUMENTS

| | | |
|---|---|---|
| AU | 613688 | 6/1989 |
| AU | 645589 | 2/1992 |
| AU | 250686 | 8/2002 |
| EP | 0556083 A1 | 8/1993 |
| WO | WO-00/41721 A1 | 7/2000 |
| WO | WO-01/30168 A1 | 5/2001 |
| WO | 2004/022196 A1 | 3/2004 |

OTHER PUBLICATIONS

Birkelund et al (New Bacterial Vaccines, 2003, pp. 93-109, abstract only).*
Kanamaru, Yoshihiro et al., "Nonspecific purification of bovine secretory IgA from normal bovine colostrum," *Research Bulletin of the Faculty of Agriculture Gifu University*, vol. 43:215-222 (1980)asd.
Kit, Y.Y. et al., "Phosphorylation of Lipids Tightly Bound to Secretory Immunoglobulin A in Antibody Fractions from Human Breast Milk Possessing Protein Kinase Activity," *Biochemistry*, vol. 63(6):719-724, Translated from *Biokhimiya*, vol. 63(6):852-858 (1998).
Kit, Y.Y. et al., "Secretory Immunoglobulins A from Human Milk Possess Affinity to Oligonucleotides and Nucleic Acids," *Biochemistry*, vol. 64(1):40-46, Translated from *Biokhimiya*, vol. 64(1):52-59 (1999).
Norcross, N.L., "Specific Defence Mechanisms of the Udder," *Flem. Vet. J.*, vol. 62(Suppl. 1):129-139 (1990).
International Search Report for Application No. PCT/AU2006/000607, dated Jun. 30, 2006.

* cited by examiner

*Primary Examiner* — Nita M Minnifield
(74) *Attorney, Agent, or Firm* — Nelson Mullins Riley & Scarborough LLP; Amy E. Mandragouras, Esq.; Briana M. Erickson (57) ABSTRACT

The invention relates to the production of compositions containing IgA for use as a food additive. More specifically, it relates to a process to prepare an IgA-enriched milk product extract composition and to such compositions.

22 Claims, 10 Drawing Sheets

Figure 1: Relative amounts of IgA:IgG in various animal products analysed by ELISA.

| Product | IgG %w/w | IgA %w/w |
|---|---|---|
| Bovine serum[1] | 20.4 | 0.4 |
| Bovine colostrum[2] | 46.4 | 5.4 |
| IgG Fraction[3] | 41 | 5 |
| Whey fraction (IgA fraction)[4] | 11 | 4.7 |

1) A sample of bovine serum which has not been fractionated.
2) A sample of bovine colostrum which has not been fractionated.
3) Immunoglobulin fraction from whey using a combined anion and cation exchange chromatography process.
4) Immunoglobulin fraction from whey using the process of the invention.

IMMUNOGLOBULIN FRACTION AND PROCESS THEREFOR

FIELD OF THE INVENTION

The invention relates to the production of compositions containing IgA for use as a food additive. More specifically, it relates to a process to prepare an IgA-enriched milk product extract composition and to such compositions.

BACKGROUND OF THE INVENTION

The present invention is to be understood in light of what has previously been done in the field. However, the following discussion is not an acknowledgment or admission that any of the material referred to was published, used or part of the common general knowledge in Australia as at the priority date of the application.

Immunoglobulin A (IgA) is the dominant immunoglobulin in human secretions, including breast milk and provides the body with protection against pathogens, binding to disease-causing viruses, bacteria, fungi and their toxins. IgA provides infants essential protection against the aforementioned pathogens. IgA antibodies are effective when taken orally because they are resistant to degradation by enzymes in the gut, thus making them ideal as nutraceuticals or food supplements. IgA may be combined with probiotics to inhibit or reduce adverse effects due to pathogens. Applications include use of IgA as a nutraceutical ingredient to target pathogens which cause infections of human mucosal surfaces such as in the nose, eyes, ears, lungs, breast and vagina. Moreover, IgA-containing products are suitable for gut and oral health applications. Due to the low levels of IgA normally present in cows' milk, the established method to increase the yield of IgA on a commercial scale is by immunisation regimes to boost the levels in the milk. Typically, cow's milk contains IgA and IgG in a ratio of approximately 1:8.

Compositions containing IgA for food consumption are currently produced globally, using essentially the same process and in virtually the same manner. The most common production methodology is referred to as a hyperimmunisation process whereby generally a number of cows are administered an immunogenic substance such as a virus to produce a hyperimmune response. As a consequence of the hyperimmune response, milk produced by the immunised cows contains increased amounts of IgA, otherwise known as "hyperimmune milk". The hyperimmune milk is then concentrated using standard membrane technology to produce a milk product extract containing around 5% w/w IgA, which can be used as a food supplement such as for infant milk formula.

An inherent problem with the procedure to produce the hyperimmune milk is that it generally takes up to three months for the immunisation regime to generate a hyperimmune response in the cows and then a further month to harvest the hyperimmune milk in sufficient quantities to produce a commercial amount of IgA-containing milk product extract. Additionally, this procedure is also expensive compared to the process of the present invention.

IgA has an acidic isoelectric point, or pI, in the range of approximately 4.5-6.5 due to variable glycosylation, and is not generally considered to be able to adsorb to cation exchange resins in an amount that would be of commercial value. The process of the present invention surprisingly allows for the fractionation of IgA from milk products such as skim milk by cation exchange chromatography by modifying the loading and elution conditions. Such a process has not previously been achieved on a commercial scale.

Moreover, the process of the present invention may be included as part of an existing process for purification of other components of milk products, such as lactoferrin, lactoperoxidase or growth factors. An example of such a process is one where milk product is contacted with the cation exchange resin and an IgA-enriched fraction is eluted first, followed by an IgA-depleted lactoperoxidase fraction and then a lactoferrin fraction by sequential elution with mobile phases of increasing ionic strength.

SUMMARY OF THE INVENTION

The invention relates to a process to prepare an IgA-enriched milk product extract composition that obviates the need for hyperimmunisation of cows and thus the time and costs involved therewith.

It is thus an object of the present invention to provide an IgA-enriched milk product extract composition and process therefor, which process can be used on a commercial scale, which overcomes at least some of the disadvantages of the prior art. The term 'IgA-enriched' means the ratio of IgA:IgG in the eluted milk product extract is increased relative to the ratio of IgA:IgG in the milk product before fractionation.

According to one aspect of the present invention, there is provided a process to prepare an IgA-enriched milk product extract composition including IgA and IgG extracted from a milk product, wherein the relative IgA to IgG content is increased compared to that in the milk product, which process includes:

providing:
a source of milk product;
a cation exchange resin; and
a mobile phase;

contacting the milk product with the cation exchange resin such that IgA is preferentially adsorbed thereon compared with IgG;

eluting the cation exchange resin with the mobile phase; and collecting the eluted IgA-enriched fraction.

It will be apparent to those skilled in the art that the milk product is not necessarily limited to whole cows' milk but other milk products can be used as a starting point in the production of an IgA-enriched milk product extract composition.

In a further aspect of the invention, there is provided a process wherein the milk product is selected from the group consisting of whole milk, skim milk, whey, and colostrum.

The particular conditions under which the IgA-enriched milkproduct extract composition is produced can be varied and still result in an IgA-enriched fraction.

Accordingly, in a preferred aspect of the invention, there is provided a process wherein elution is performed with a mobile phase containing 0.05-0.4M NaCl (0.29-2.34% w/v) or equivalent ionic strength, preferably 0.08-0.35M NaCl (0.47-2.05% w/v), more preferably about 0.17M NaCl (1% w/v) or equivalent ionic strength. Other suitable mobile phase solutions of equivalent ionic strength may be used in the alternative.

In another aspect of the invention the mobile phase has a pH in the range of 4.5-9, preferably 5.5-7.5, most preferably a pH of about 6.5.

In another aspect of the invention, the flow rate at which the milk product is adsorbed to the cation exchange column during the contact step, may be in the range of 6-90 liters per liter of resin per hour (h) (linear flow 60-900 cm per h). Preferably the flow rates used are in the range of 6-70 liters per liter of resin per hour (linear flow 60-700 cm per h), more preferably 6-40 liters per liter of resin per hour (linear flow 60-400 cm per h). With these flow rates it has been found that for optimum fractionation of IgA the amount of milk product in contact with the cation exchange resin is in the range of about 16-300 column (bed) volumes, preferably 16-200 column volumes, more preferably 16-40 column volumes.

In a further aspect of the invention, prior to elution of the IgA-enriched fraction, the cation exchange resin is rinsed with a buffer of low ionic strength, (<0.008 M salt or its equivalent) or water, to remove milk product remaining in the column.

Moreover, various types of cation exchange resins may be employed in the present invention, of which SEPHAROSE® (cross-linked agarose; GE Healthcare) cation exchange resin beads, such as SP SEPHAROSE® Big Beads, are preferred. Further preferred are resin beads in the size range 45-300 μm.

In a further aspect of the invention, there is provided a process wherein the cationic exchange resin comprises SEPHAROSE® beads, preferably in the size range 45-300 μm.

The process of the invention may be employed as a continuous process or as a batch process, with continuous processing being preferred. The eluted IgA-enriched fraction may be subsequently treated to reduce the salt content therein.

Skim milk contains about 1-2.5% IgG w/w and 0.05-0.1% IgA w/w and bovine serum contains 20% IgG w/w and 0.4% IgA w/w. The inventors have found that with the process of the present invention the milk product extract concentrate (eluate) obtained surprisingly contains lower levels of IgG w/w than expected, with ratios of IgA:IgG typically in the order of 1:2 which equates to an eight- to sixteen-fold concentration of IgA. The quantitation of IgA and IgG was performed using an ELISA (enzyme linked immunosorbent assay) kit. This increase in IgA:IgG ratio has significant implications for those wanting to provide increased levels of IgA in food substances or as neutraceuticals. The presence of IgA and the relative amounts (ratio) of IgA and IgG in cation exchange chromatography eluates was not previously known.

Accordingly, a further aspect of the invention provides for a process in which the resulting IgA-enriched milk product extract composition comprises an IgA:IgG ratio of at least 1:8, preferably 1:4, and more preferably at least 1:2.

The IgA enriched milk product extract composition may be further treated to reduce the amount of non-IgA proteins present. This may be achieved by membrane filtration, column chromatography, dialysis or other known means. Removal of such extraneous proteins may be considered important for the production of standardised food substances or nutraceuticals.

In another aspect of the invention there is provided an IgA-enriched milk product extract composition in which the IgA:IgG ratio is at least 1:8, preferably 1:4, and more preferably at least 1:2.

According to a further aspect of the invention there is provided an IgA-enriched milk product extract composition, obtained by the process of the invention. Moreover, the milk product extract of the invention may be used as a food substance or nutraceutical, preferably as an infant food substance or nutraceutical.

The results of the present process are particularly surprising given that immunoglobulins are considered to belong to a class of proteins with an acidic isoelectric point and therefore unlikely to be retained on a cation exchange resin, or in a manner in which IgA is preferentially bound compared to IgG.

It will be appreciated that the present invention described herein should not be limited to specific examples of features disclosed.

DETAILED DESCRIPTION

The following is a detailed description of the preparation of an IgA-enriched fraction of the present invention.

Suitable sources of IgA may include milk products such as whole milk, skim milk, whey or colostrum from a mammal such as man, cow, sheep, goat, sow or the like. In contacting the milk product with the cation exchange resin to allow the IgA to adsorb, the pH of the milk product is preferably about 6.5 although it is not necessary to adjust the pH of the milk product for the present invention.

The flow rates used to contact the milk product with the cation exchange resin can be varied over a wide range, such as from 6-90 liters per liter resin per hour (linear flow 60-900 cm per h), preferably, 6-70 liters per liter resin per hour (linear flow 60-700 cm per h), more preferably about 6-40 liters per liter resin per hour (linear flow 60-400 cm per h). The lower limit is determined by cost-effectiveness for an industrial process, whereby at very low flow rates the cost to run the process exceeds the return. High flow rates are suitable for IgA purification provided the total amount of milk product contacted with the resin is limited.

Whilst milk product volumes greatly exceeding the resin volume are suitable for purification of other milk products such as lactoperoxidase and lactoferrin, as described in Australian Patent no. 613688, the present inventors have found that a milk product volume to resin volume in the order of 1000 column volumes (liters milk product per liter resin) is unsuitable for IgA purification by the process of the invention. The inventors have found that milk product volume to resin volume in excess of about 400 column volumes result in little IgA binding to the resin and the IgA recovered will not be enriched relative to IgG in the starting material. The preferred upper limit according to the invention, in the case of skim milk, is about 300 column volumes, preferably about 200 column volumes, most preferably about 34 column volumes. As the milk product to resin ratio increases the amount of IgA bound and the purity of the eluted IgA gradually decreases. As for the flow rate, the lower limit is set by commercial concerns rather than column-related factors. If the volume of milk product loaded declines much below 16 column volumes, a point is reached where the rinse and elution times exceed the point where sufficient IgA can be purified to make the process economically viable.

Following the step of loading the cation exchange column with milk product, and prior to elution of the IgA with the mobile phase, the unbound milk product within the cation exchange column may be removed by rinsing the column with water or a buffer having an ionic strength of less than, for example, 0.0086M sodium chloride.

In eluting the adsorbed IgA, a mobile phase consisting of a buffer solution having a low ionic strength of 0.086-0.4M sodium chloride, potassium chloride, or equivalent is used. The type of salt used in the mobile phase is not limited. As the ionic strength increases above 0.4, the purity of the IgA decreases as non-IgA proteins begin to elute, thus diluting the IgA with other proteins. Preferably, an ionic strength equivalent to 0.35M sodium chloride or less is used.

The mobile phase may have a pH within a broad range, such as 4.5-9.0, preferably 5.5-7.5, most preferably about 6.5. At the upper and lower limits both protein stability and the ability of proteins to bind to the cation exchange resin become influenced. A pH in the range 5.5-7.5 provides the highest IgA purity without lowering yields.

In the present invention, the type of cation exchange resin suitable for adsorption of IgA may include resins such as SEPHAROSE® cation exchange resin beads. For example, SP SEPHAROSE® Big Beads and CM SEPHAROSE® beads (products of GE Healthcare) which contain sulfopropyl functional groups and carboxymethyl groups, respectively, are suitable. The size of the cation exchange resin beads is preferably in the range from 45-300 μm. Both SP SEPHAROSE® beads in the range 45-165 μm and in the range 100-300 μm are suitable for IgA adsorption and purification according to the invention.

One of the further treatments to which the IgA-enriched milk product extract composition can be subjected is desalting by, for example, dialysis or ultrafiltration. Another treatment to which the IgA-enriched milk product extract composition can be subjected is the removal of non-IgA proteins. The removal of non-IgA proteins may be achieved by further chromatography by, for example, immunoadsorption or size-exclusion.

The IgA-enriched milk product extract composition of the invention may be used as a food substance or nutraceutical, preferably as in infant food substance or nutraceutical.

The process of the invention may be performed in isolation to prepare an IgA-enriched milk product extract composition, or may be incorporated as part of an integrated fractionation process in which other desired milk product extracts are fractionated.

Process for Producing IgA-Enriched Fraction & IgA-Depleted Fraction

A preferred method of the invention is to pack a 10 cm deep column of SP (sulfopropyl) SEPHAROSE® of greater than 45 μM (ideally 90-300 μM). To the column a flow of a dairy product, ideally skimmed milk, is applied at 11 ml/min (linear flow 331 cm/h or 0.55 column volumes (CV)/min) until the volume of milk applied is 134.6 times the volume of the resin packed into the column. The milk remaining in the column is removed with 2.5 CV of a buffer of low ionic strength (<0.05% (0.0086M) NaCl or equivalent), or water at 3.5 ml/min (linear flow 147 cm/h or 0.25 CV/min) for 10 min. The IgA-enriched fraction is eluted from the column with 3.5 CV of a buffer containing sodium ions equivalent to 1% (0.171M) NaCl, pH 6.5, by flowing the cation solution at 3.5 ml/min (linear flow 102 cm/h or 0.175 CV/min) for 20 min. The first 3 min (0.5 CV) will be discarded to drain and the next 20 min (3.5 CV) collected as the IgA-enriched fraction (including 3 min [0.5 CV] overlapping the application time of the next buffer ie breakthrough time). The remaining protein (IgA-depleted fraction) is eluted from the column with 3.5 CV of a buffer containing sodium ions equivalent to 8.75% (1.5M) NaCl by flowing the cation solution at 3.5 ml/min (linear flow 102 cm/h or 0.175 CV/min) for 20 min. The first 3 min (0.5 CV) will be discarded to drain and the next 20 min (3.5 CV) collected as the IgA-depleted fraction (including 3 min [0.5 CV] overlapping the application time of the next buffer ie breakthrough time). The protein fractions recovered are diafiltered through an ultrafiltration membrane or equivalent to remove salt. It would be clear to a person skilled in the art that this IgA fractionation method can be scaled up for commercial use.

Process for Producing Three Fractions (IgA-Enriched Fraction, IgA-Depleted Lactoperoxidase and Lactoferrin)

A further preferred method of the invention is to pack a 10 cm deep column of SP (sulphopropyl) SEPHAROSE® of greater than 45 μM (ideally 90-300 μM). To the column a flow of a dairy product, preferably skimmed milk, is applied at 11 ml/min (linear flow 331 cm/h or 0.55 CV/min) until the volume of milk applied is 134.6 times the volume of the resin packed into the column. The milk remaining in the column is removed with 2.5 CV of a buffer of low ionic strength (<0.008M NaCl or equivalent), or water at 3.5 ml/min (linear flow 147 cm/h or 0.25 CV/min) for 10 min. The IgA-enriched fraction is eluted from the column with 3.5 CV of a buffer containing sodium ions equivalent to 1% (0.171M) NaCl, pH 6.5, by flowing the cation solution at 3.5 ml/min (linear flow 102 cm/h or 0.175 CV/min) for 20 min. The first 3 min (0.5 CV) will be discarded to drain and the next 20 min (3.5 CV) collected as the IgA-enriched fraction (including 3 min [0.5 CV] overlapping the application time of the next buffer ie breakthrough time). The IgA-depleted lactoperoxidase fraction is eluted from the column with 3.5 CV of a buffer containing sodium ions equivalent to 2.5% w/v (0.43 M) NaCl (though other cations would be suitable) by flowing the cation solution at 3.5 ml/min (linear flow 102 cm/h or 0.175 CV/min) for 20 min. The first 3 min (0.5 CV) will be discarded to drain and the next 20 min (3.5 CV) collected as the IgA-depleted lactoperoxidase fraction (including 3 min [0.5 CV] overlapping the application time of the next buffer ie breakthrough time). The lactoferrin fraction is eluted from the column with 3.5 CV of a buffer containing sodium ions equivalent to 8.75% (1.5 M) NaCl by flowing the cation solution at 3.5 ml/min (linear flow 102 cm/h or 0.175 CV/min) for 20 min. The first 3 min (0.5 CV) will be discarded to drain and the next 20 min (3.5 CV) collected as the lactoferrin fraction (including 3 min [0.5 CV] overlapping the application time of the next buffer ie breakthrough time). The protein fractions recovered are diafiltered through an ultrafiltration membrane or equivalent to remove salt. It would be clear to a person skilled in the art that this IgA fractionation method can be scaled up for commercial use.

The present invention is hereinafter described with reference to the Examples.

EXAMPLE 1

Preparation of an IgA-Enriched Fraction from Skim Milk

Figure 1:
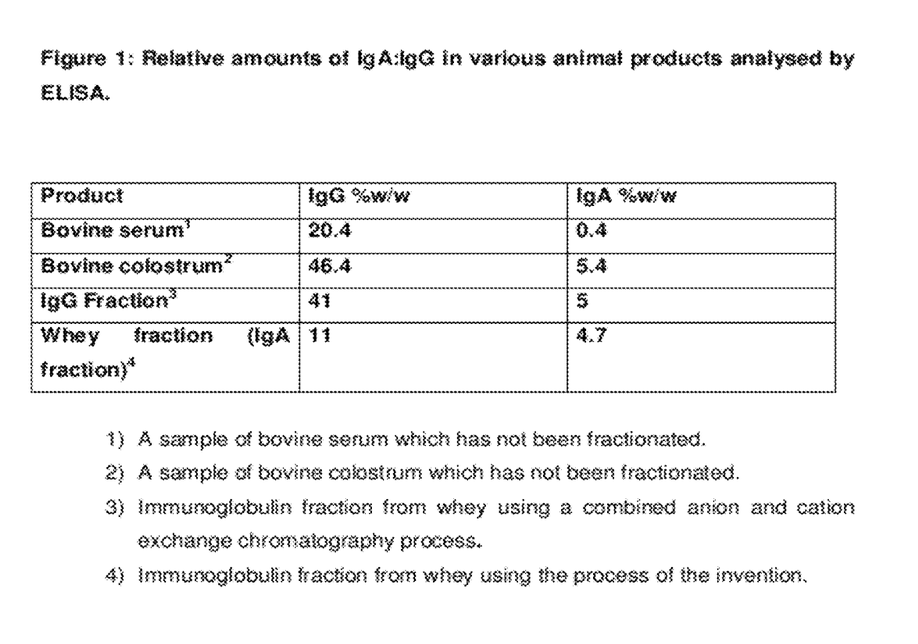
FIG. 1—IgA:IgG in various animal products analysed by ELISA.

In a preferred process according to the invention, skim milk is loaded in a continuous process onto multiple SP SEPHAROSE® Big Beads cation exchange resin columns, each of a bed volume of 29.7 liters, at a flow rate of 22 liters per liter resin per hour, a total of 134.6 column volumes. The column is then rinsed with a buffer of low ionic strength (water), and eluted with a mobile phase consisting of 0.3M NaCl, pH 6.5. The eluted IgA-enriched fraction is collected and dialized to reduce the salt content. The eluted fraction was analysed for immunoglobulin content by ELISA and found to contain 4.7% w/w IgA and an IgA:IgG ratio of approximately 1:2 (FIG. 1). The fractionated IgA-enriched milk product extract composition may then be freeze-dried and stored in a stable state at 15° C.

EXAMPLE 2

Effect of Salt Concentration and Flow Rate of Elution on IgA Elution

Figure 2A:
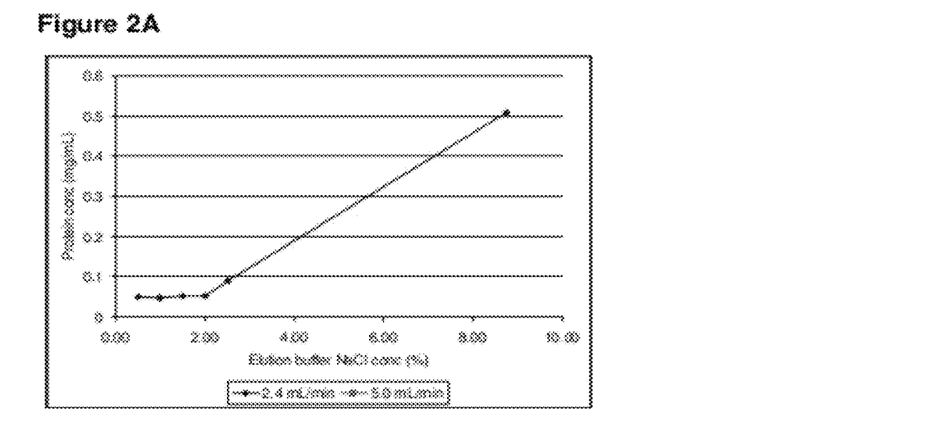
FIGS. 2A-2C—Effect of Salt concentration and flow rate of elution on IgA elution.
Figure 2B:
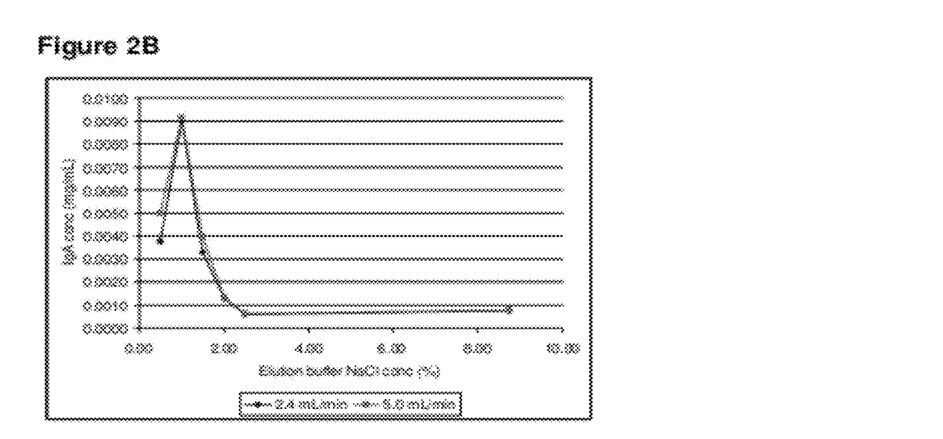
Figure 2C:
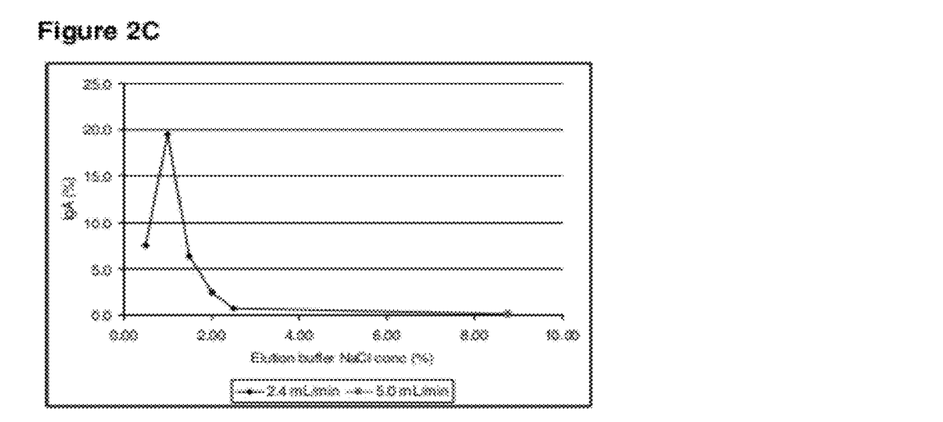

IgA-spiked skim milk was passed through a column packed with SP SEPHAROSE® Big Beads (GE Healthcare) 90-300 μm, at a flow rate of 11 ml/min to allow the resin to adsorb an IgA-containing fraction of the skim milk. A total of 134.6 column volumes (CV) were passed through the column. Deionised water was passed through the column at a flow rate of 5 ml/min to rinse the resin, and then a mobile phase containing one of 0.5, 1, 1.5, 2, 2.5, or 8.75% NaCl, pH 6.5, was passed through the column at a flow rate of either 2.4 or 5.0 ml/min to elute an IgA-containing fraction. The total protein concentration of the eluted fraction (FIG. 2A), the IgA concentration (FIG. 2B) and IgA % (FIG. 2C) in the eluted fraction were determined. At ionic strengths above 2% w/v NaCl, increased amounts of non-IgA protein elute from the column with no additional IgA eluted. There was no difference in IgA concentration in the eluted fraction when the elution flow rate was 2.4 ml/min or 5 ml/min.

EXAMPLE 3

Effect of Milk Product Volume Contacted with Cation Exchange Resin

Figure 3A:
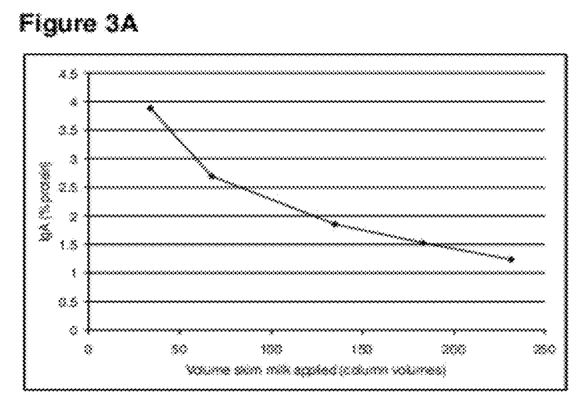
FIGS. 3A-3E—Effect of milk product volume contacted with cation exchange resin.
Figure 3B:
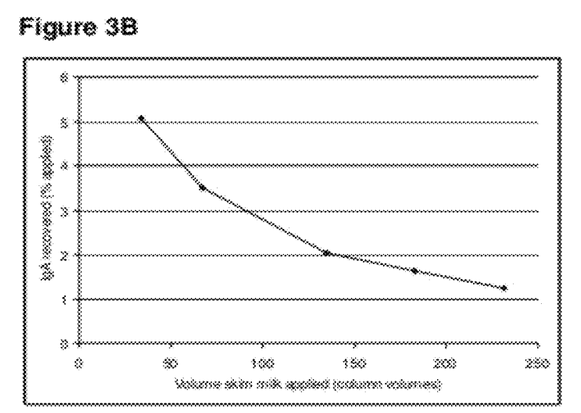
Figure 3C:
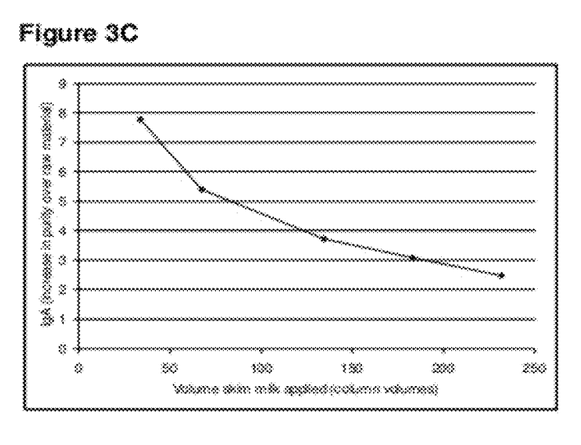
Figure 3D:
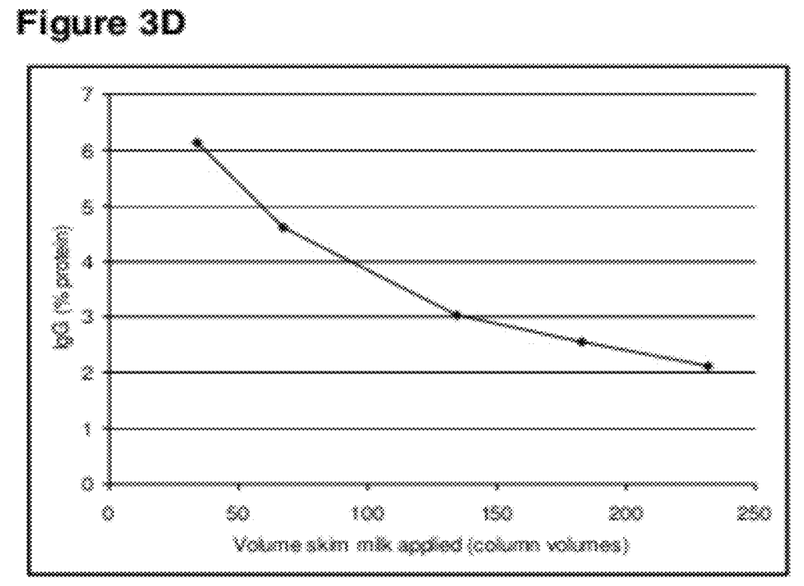
Figure 3E:
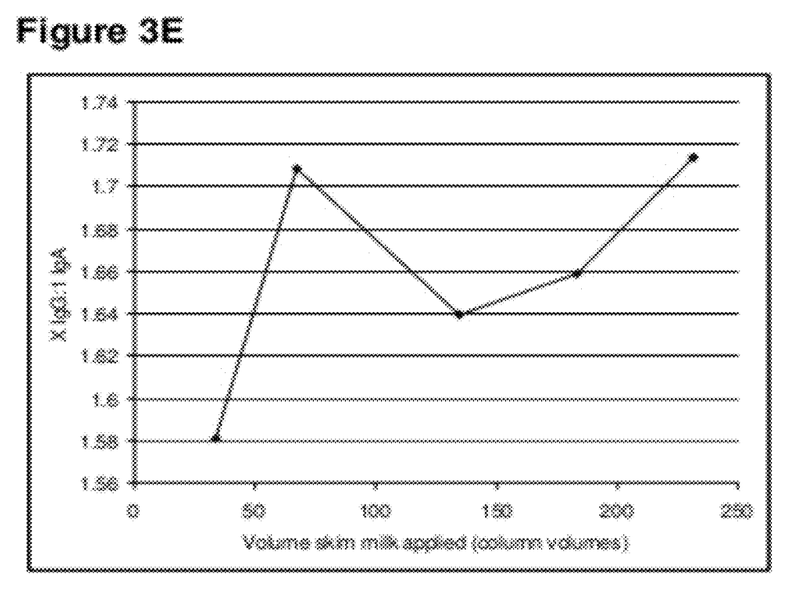

Skim milk was passed through a column packed with SP SEPHAROSE®Big Beads (GE Healthcare) 90-300 μm, at a flow rate of 11 ml/min to allow the resin to adsorb proteins from the skim milk. The amount of skim passed was increased while maintaining the amount of resin. Five volumes of skim milk, corresponding to 33.6 (676 ml), 67.3 (1352 ml), 134.6 (2705 ml), 183.0 (3678 ml), and 231.5 (4652 ml) CV, were tested. Deionised water was passed through the column at a flow rate of 5 ml/min to rinse the resin, and then a mobile phase containing 8.75% (1.5M) NaCl, pH 6.5, was passed through the column at a flow rate of 3.5 ml/min to elute total protein adsorbed to the resin. The amount of IgA and IgG in the eluted fractions was determined relative to the total protein recovered. The proportion of the total protein that eluted as IgA reduced as the volume of skim milk increased (FIG. 3A and FIG. 3B). The purity of IgA recovered decreased with increasing volumes of skim milk (FIG. 3C). Moreover, the amount of IgG recovered as a percentage of total protein decreased with increasing volumes of skim milk (FIG. 3D), although the ratio of IgA:IgG remained between 1:1.58 and 1:1.71 (FIG. 3E). These data suggests that increasing the amount of milk product passed through the resin decreases the amount of IgA and the IgA as a proportion of the total protein but still yields high IgA:IgG ratios, reflecting proportional decreases in yields of both IgA and IgG.

EXAMPLE 4

Effect of Skim Milk Product Volume Contacted with Cation Exchange Resin

Figure 4A:
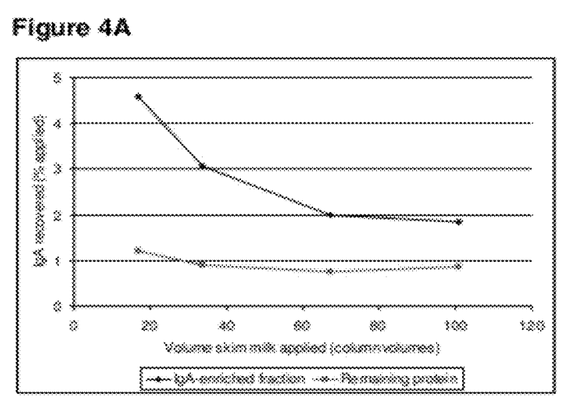
FIGS. 4A-4C—Effect of skim milk product volume contacted with cation exchange resin.
Figure 4B:
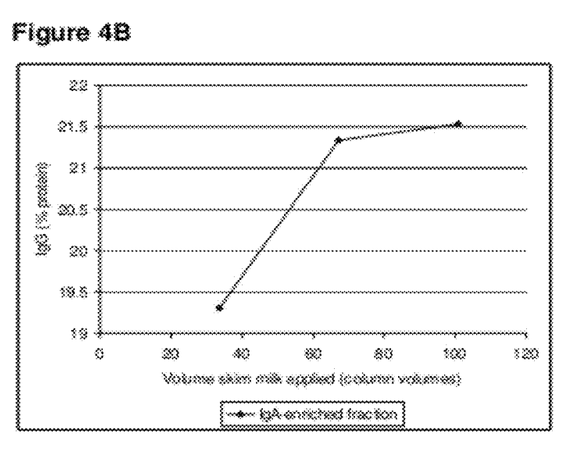
Figure 4C:
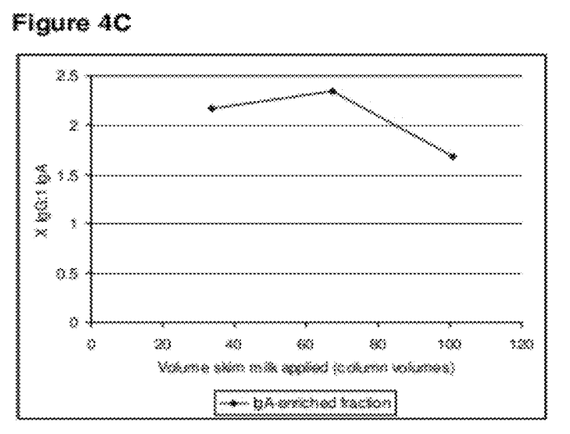

Skim milk was passed through a column packed with SP SEPHAROSE® Big Beads (GE Healthcare) 90-300 μm, at a flow rate of 11 ml/min to allow the resin to adsorb proteins from the skim milk. The amount of skim passed was increased while maintaining the amount of resin. Five volumes of skim milk, corresponding to 16.8 (338 ml), 33.6 (676 ml), 67.3 (1352 ml), and 100.9 (2028 ml) CV, were tested. Deionised water was passed through the column at a flow rate of 5 ml/min to rinse the resin, the IgA-enriched fraction was eluted with a mobile phase containing 0.192M $Na^+$ (0.84% disodium hydrogen orthophosphate+0.89% NaCl (pH 6.5)) at a flow of 3.5 ml/min and then a mobile phase containing 8.75% (1.5M) NaCl, pH 6.5, was passed through the column at a flow rate of 3.5 ml/min to elute the remaining protein adsorbed to the resin. The amount of IgA and IgG in the eluted fractions was determined relative to the total protein recovered. The proportion of the total protein that eluted as IgA reduced as the volume of skim milk increased (FIG. 4A and FIG. 4B). Increasing the volume of skim milk applied to the column lowered the recovery of the applied IgA. The IgA:IgG ratio remained approximately 1:2 as the volume of skim milk applied increased (FIG. 4C).

EXAMPLE 5

Effect of Mobile Phase pH on the Composition of IgA Eluted

Figure 5A:
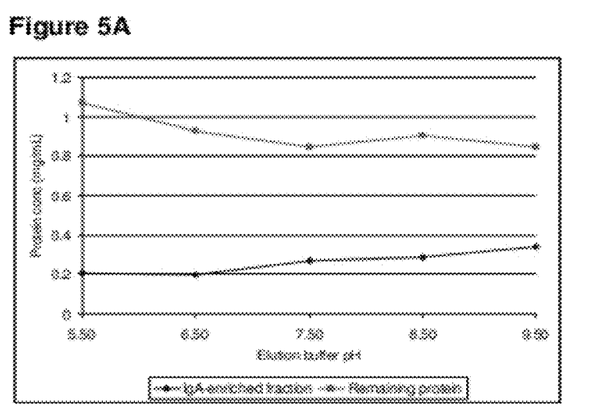
FIGS. 5A-5D—Effect of mobile phase pH on the composition of IgA eluted.
Figure 5B:
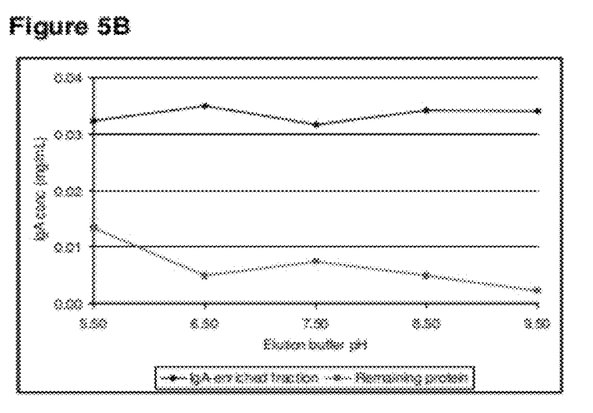
Figure 5C:
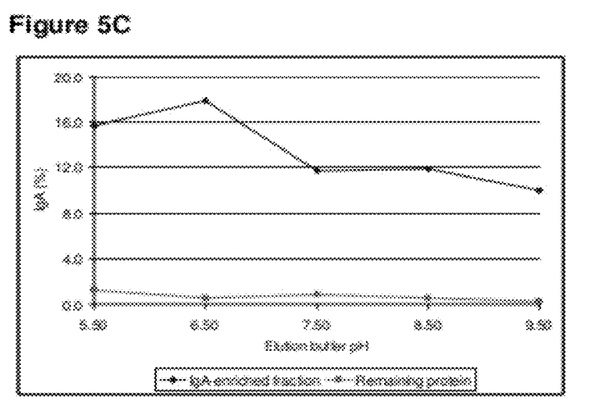
Figure 5D:
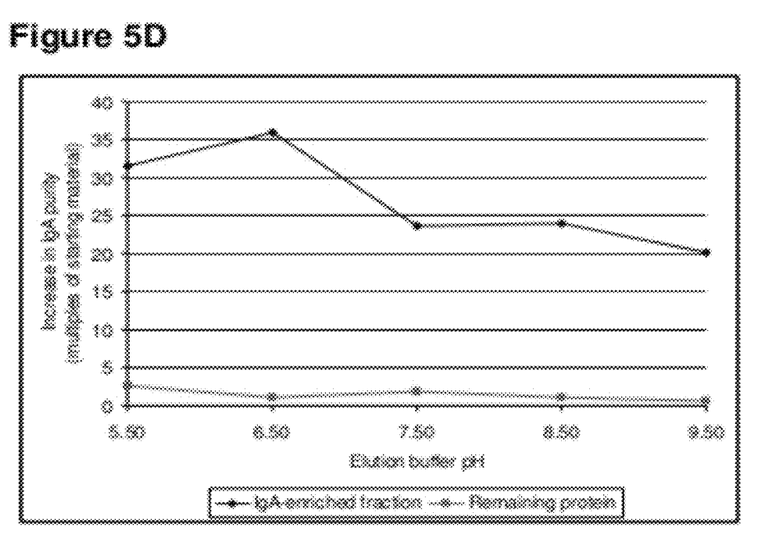

Skim milk was passed through a column packed with SP SEPHAROSE® Big Beads (GE Healthcare) 90-300 μm, at a flow rate of 11 ml/min to allow the resin to adsorb an IgA-containing fraction of the skim milk. The volume of skim milk passed through the column was 33.6 CV. Deionised water was passed through the column at a flow rate of 5 ml/min to rinse the resin, and then a mobile phase of ionic strength equivalent to 1.125% (0.19M) NaCl, at pH 5.5, 6.5, 7.5, 8.5, or 9.5 was passed through the column at a flow rate of 3.5 ml/min to elute an IgA-containing fraction and then a mobile phase containing 8.75% (1.5M) NaCl, pH 6.5, was passed through the column at a flow rate of 3.5 ml/min to elute the remaining protein adsorbed to the resin. The total protein concentration of the eluted fraction (FIG. 5A), the IgA concentration (FIG. 5B), the IgA % (FIG. 5C), and increase in IgA purity relative to the starting milk product (FIG. 5D) in the eluted fraction were determined. As the pH increased above 6.5, increased amounts of non-IgA protein eluted from the column with no additional IgA eluted. Moreover, the IgA % in the eluted fraction decreased with increasing pH, 18% at pH 6.5 down to about 10% at pH 9.5, and the purity of the IgA fraction also declined at pH above 6.5. The IgA:IgG ratio was >1:1.5, >1:1.4, >1:1.5, >1:1.4, and >1:1.4 at pH of 5.5, 6.5, 7.5, 8.5, and 9.5, respectively.

EXAMPLE 6

IgA Purification from Whey Protein Concentrate (WPC)

Figure 6A:
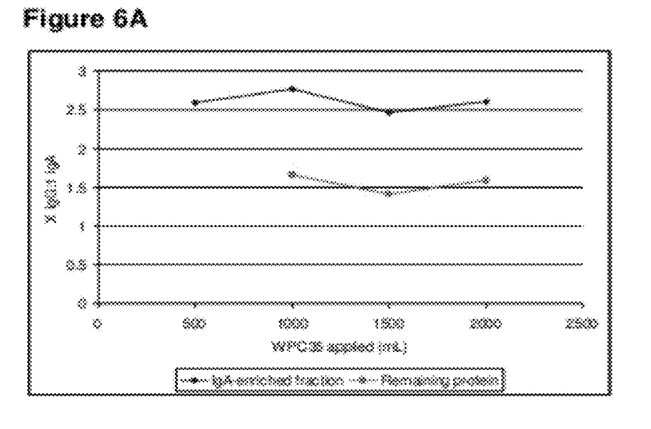
FIGS. 6A-6C—IgA purification from whey protein concentrate (WPC).
Figure 6B:
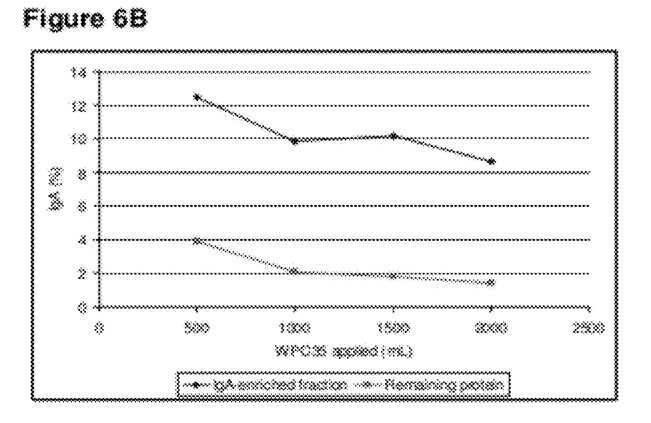
Figure 6C:
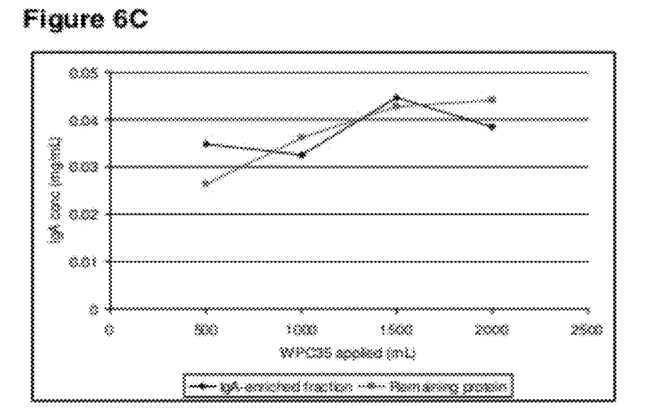

Whey protein concentrate (WPC) was passed through a column packed with SP SEPHAROSE® Big Beads (GE Healthcare) 90-300 μm, at a flow rate of 11 ml/min to allow the resin to adsorb proteins from the WPC. The amount of WPC passed was increased while maintaining the amount of resin. Four volumes of WPC were passed through the column corresponding to 25 (500 ml), 50 (1000 ml), 75 (1500 ml), and 100 (2000 ml) CV of WPC. Deionised water was passed through the column at a flow rate of 5 ml/min to rinse the resin, and then a mobile phase of ionic strength equivalent to 1.125% (0.19M) NaCl, at pH 7.5, was passed through the column at a flow rate of 3.5 ml/min to elute an IgA-containing fraction and then an un-buffered mobile phase containing 8.75% (1.5M) NaCl was passed through the column at a flow rate of 3.5 ml/min to elute the remaining protein adsorbed to the resin. The amount of IgA and IgG in the eluted fractions was determined relative to the total protein recovered. The proportion of the total protein that eluted as IgA reduced as the WPC volume increased (FIG. 6A). Applying increasing amounts of WPC results in lower IgA (% protein) (FIG. 6B), but more IgA in total (FIG. 6C). WPC volumes corresponding to 25, 50, 75, and 100 CV yielded IgA:IgG ratios of 1:2.59, 1:2.76, 1:2.471, and 1:2.61, respectively.

EXAMPLE 7

A Process to Isolate IgA-Enriched Fraction, Lactoferrin and Lactoperoxidase; Effect of Mobile Phase Ionic Strength on IgA in Various Fractions Skim milk (134.6 CV) was passed through a column packed with SP SEPHAROSE® Big Beads (GE Healthcare) 90-300 µm, at a flow rate of 11 ml/min to allow the resin to adsorb proteins from the skim milk. The milk remaining in the column was removed with 2.5 CV of deionised water at 5 ml/min (linear flow 147 cm/h or 0.25 CV/min) for 10 min. The IgA-enriched fraction was eluted from the column with 3.5 CV of a buffer at pH 6.5 containing 0.04M disodium hydrogen orthophosphate and NaCl to provide sodium ions equivalent to 1% w/v (0.171M) NaCl or 1.125% (0.193M) w/v NaCl, by flowing the mobile phase at 3.5 ml/min (linear flow 102 cm/h or 0.175 CV/min) for 20 min. The first 3 min (0.5 CV) were discarded to drain and the next 20 min (3.5 CV) collected as the IgA-enriched fraction (including 3 min [0.5 CV] overlapping the application time of the next buffer ie breakthrough time). The second fraction, IgA-depleted lactoperoxidase, was eluted from the column with 3.5 CV of a buffer containing sodium ions equivalent to 2.5% w/v (0.43 M) NaCl, pH 6.5, by flowing the cation solution at 3.5 ml/min (linear flow 102 cm/h or 0.175 CV/min) for 20 min. The first 3 min (0.5 CV) was discarded to drain and the next 20 min (3.5 CV) collected as the IgA-depleted lactoperoxidase fraction (including 3 min [0.5 CV] overlapping the application time of the next buffer ie breakthrough time). The lactoferrin fraction was eluted from the column with 3.5 CV of a buffer containing sodium ions equivalent to 8.75% w/v (1.5 M) NaCl, pH 6.5, by flowing the cation solution at 3.5 ml/min (linear flow 102 cm/h or 0.175 CV/min) for 20 min. The first 3 min (0.5 CV) was discarded to drain and the next 20 min (3.5 CV) collected as the lactoferrin fraction (including 3 min [0.5 CV] overlapping the application time of the next buffer ie breakthrough time). The protein fractions recovered were assayed for IgA, IgG and growth factor IGF1 content.

Figure 7A:
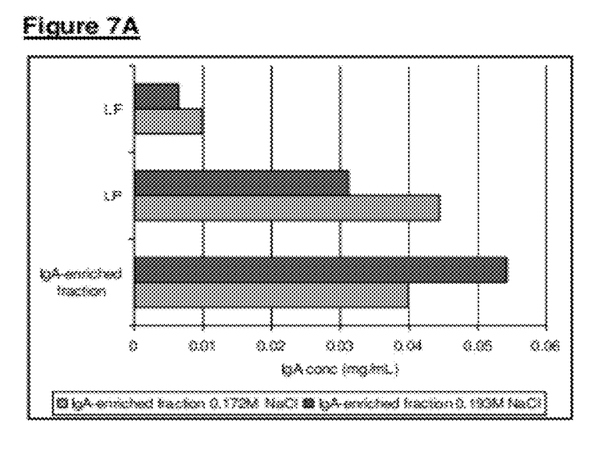
FIGS. 7A-7E—A process to isolate IgA-enriched fraction, lactoferrin and lactoperoxidase; effect of mobile phase ionic strength on IgA in various fractions.
Figure 7B:
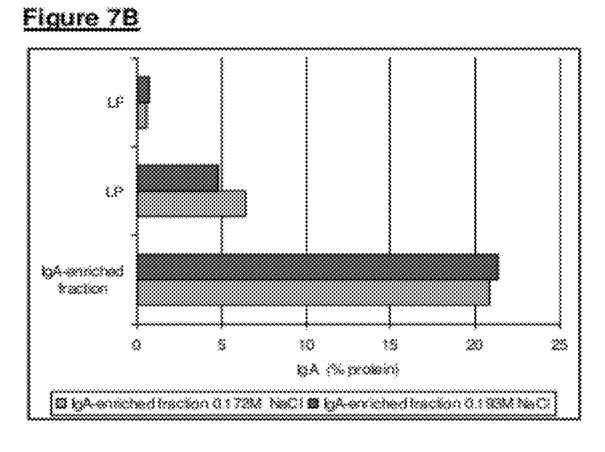
Figure 7C:
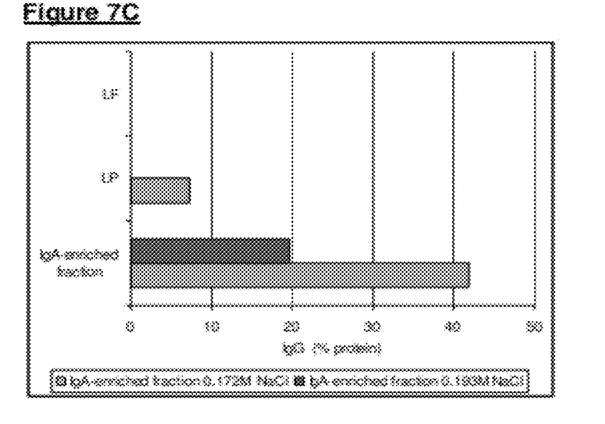
Figure 7D:
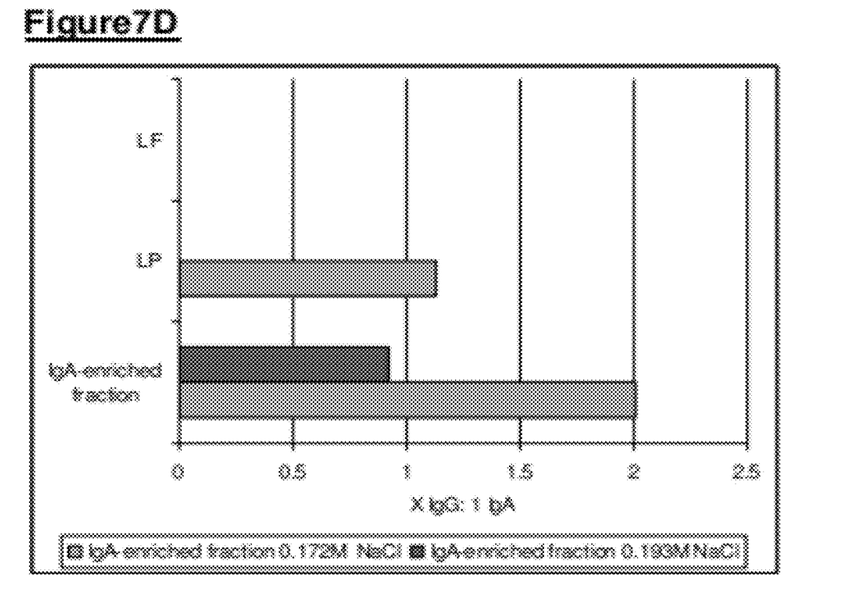

Elution with 1.125% w/v NaCl increased the amount of IgA in the IgA-enriched fraction and greatly reduced the amount of IgA present in the subsequent fractions (lactoperoxidase and lactoferrin), (FIG. 7A,7B) relative to 1% w/v NaCl. Moreover, the amount of IgG in the IgA-enriched fraction was reduced by 50% by elution with 1.125% w/v NaCl (FIG. 7C). The IgA:IgG ratio was also greatly increased by elution at the higher NaCl concentration (FIG. 7D). Elution of IgA with 0.172M NaCl and 0.193M NaCl yielded a fraction with an IgA:IgG ratio of 1:2.01 and 1:0.92, respectively.

Figure 7E:
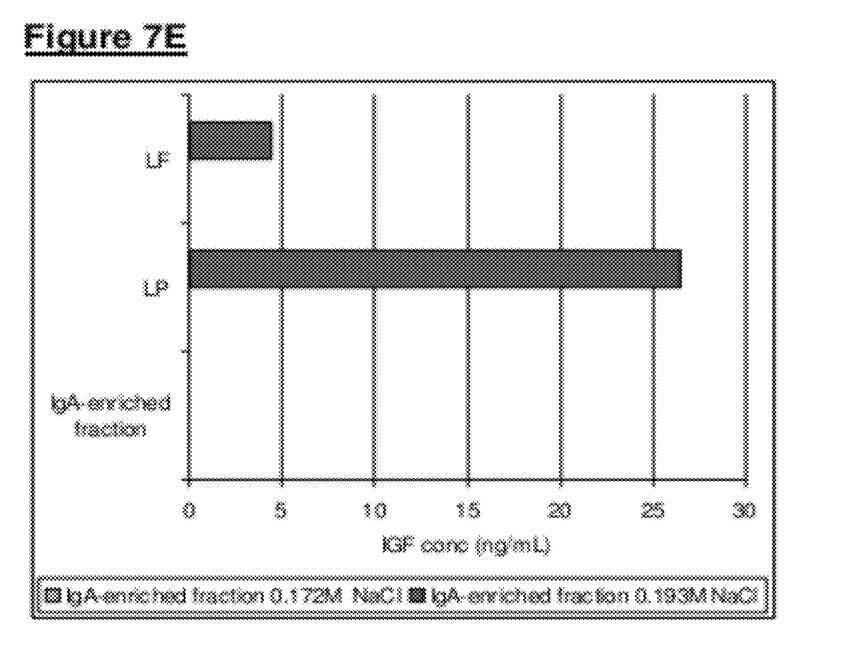

Interestingly there was no IGF1 in the IgA-enriched fraction (FIG. 7E). Very little lactoperoxidase was found in the IgA enriched fraction (<0.005% w/v in both 0.172M and 0.193M NaCl) and lactoferrin fraction (<0.005% w/v in both 0.172M and 0.193M NaCl) but large amounts were found in the lactoperoxidase fraction (0.074% w/v in 0.172M NaCl and 0.073% w/v 0.193M NaCl). Little lactoferrin was found in the IgA enriched fraction (0.02 mg/ml in 0.172M NaCl and 0.06 mg/ml in 0.193M NaCl) and lactoperoxidase fraction (0.01 mg/ml in 0.172M NaCl and 0.03 mg/ml in 0.193M NaCl) but large amounts were found in the lactoferrin fraction (3.0% w/v in both 0.172M NaCl and 0.193M NaCl).

The claims defining the invention are as follows:

1. An industrial scale process to prepare an IgA-enriched bovine milk product extract composition comprising, providing
   (i) a source of milk product selected from the group consisting of whole milk, skim milk, and whey;
   (ii) a cation exchange resin; and
   (iii) a mobile phase containing 0.05-0.35M NaCl (0.29-2.05% w/v) or equivalent ionic strength;
   contacting about 16 column volumes to about 300 column volumes of the milk product with the cation exchange resin;
   eluting an IgA-enriched fraction from the cation exchange resin with the mobile phase; and
   collecting the eluted IgA-enriched fraction, wherein the relative IgA to IgG content in said composition is at least 1:4.

2. The process according to claim 1, wherein the amount of milk product contacted with the cation exchange resin is about 16 column volumes to about 40 column volumes.

3. The process according to claim 1, wherein, prior to elution of the IgA-enriched fraction, the cation exchange resin is rinsed with a buffer of low ionic strength of less than 0.008M salt or its equivalent, or water, to remove unbound milk product remaining in the column.

4. The process according to claim 1, wherein elution is with a mobile phase containing 0.17M NaCl (1% w/v) or equivalent ionic strength.

5. The process according to claim 1, wherein elution is with a mobile phase of pH in the range 5.5-7.5.

6. The process according to claim 1, wherein the cation exchange resin comprises Sepharose beads.

7. The process of claim 6 wherein the Sepharose beads are in the size range 45-300 µm.

8. The process according to claim 1, wherein, during the contacting step, the cation exchange resin is subject to a flow rate in the range of about 6-90 liters per liter resin per hour.

9. The process of claim 8 wherein the contact flow rate is in the range of about 6-70 liters per liter resin per hour.

10. The process of claim 8 wherein the contact flow rate is in the range of about 6-40 liters per liter resin per hour.

11. The process according to claim 1 wherein the process is a continuous process or a batch process.

12. The process according to claim 1 wherein the process is a continuous process.

13. The process according to claim 1 whereby the resulting IgA-enriched milk product extract composition comprises an IgA to IgG ratio of at least 1:2.

14. The process according to claim 1 whereby the resulting IgA-enriched milk product extract composition comprises an IgA content of at least 10% w/w.

15. The process according to claim 1 wherein the IgA-enriched milk product extract composition is further treated to reduce the amount of non-IgA proteins and/or salt present.

16. An IgA-enriched bovine milk product extract composition from whole milk, skim milk or whey, obtained by the process of claim 1, wherein the IgA to IgG ratio is at least 1:4, and the IgA content is at least 10% w/w.

17. The process according to claim 1, wherein the resulting IgA-enriched milk product extract composition comprises an IgA content of at least 20% w/w.

18. The IgA-enriched milk product extract composition of claim 16, wherein the IgA to IgG ratio is at least 1:2.

19. The IgA-enriched milk product extract composition of claim 16, wherein the IgA content is at least 20% w/w.

20. A food substance or nutraceutical comprising the IgA-enriched milk product extract composition of claim 16, 18 or 19.

21. The food substance or nutraceutical of claim 20, which is an infant food substance or nutraceutical.

22. A method for the treatment or prophylaxis of a disease caused by viral, bacterial, or fungal infection of a mucosal surface in a subject, comprising administering to the subject an effective amount of the IgA-enriched milk product extract composition of claim 16, 18 or 19.

\* \* \* \* \*